United States Patent
Lustig et al.

(10) Patent No.: US 8,877,973 B2
(45) Date of Patent: Nov. 4, 2014

(54) PROCESS FOR THE SYNTHESIS OF CHOLINE SALTS

(75) Inventors: Steven Raymond Lustig, Landenberg, PA (US); Dennis A. Redder, Hockessin, DE (US)

(73) Assignee: E I du Pont de Nemours and Company, Wilmington, DE (US)

( * ) Notice: Subject to any disclaimer, the term of this patent is extended or adjusted under 35 U.S.C. 154(b) by 28 days.

(21) Appl. No.: 13/515,954

(22) PCT Filed: Dec. 21, 2010

(86) PCT No.: PCT/US2010/061415
§ 371 (c)(1),
(2), (4) Date: Jun. 14, 2012

(87) PCT Pub. No.: WO2011/084765
PCT Pub. Date: Jul. 14, 2011

(65) Prior Publication Data
US 2013/0165694 A1    Jun. 27, 2013

Related U.S. Application Data

(60) Provisional application No. 61/288,368, filed on Dec. 21, 2009.

(51) Int. Cl.
| C07C 215/08 | (2006.01) |
| C07C 59/00 | (2006.01) |
| C07C 213/08 | (2006.01) |
| C07C 213/10 | (2006.01) |
| C07C 51/41 | (2006.01) |

(52) U.S. Cl.
CPC ........... C07C 213/08 (2013.01); C07C 213/10 (2013.01); C07C 51/412 (2013.01)
USPC .......................................... 564/292; 562/579

(58) Field of Classification Search
USPC .......................................... 562/579; 564/292
See application file for complete search history.

(56) References Cited

U.S. PATENT DOCUMENTS

| 2,589,840 A | 3/1952 | Meyer |
| 3,522,296 A | 7/1970 | Nagy |
| 7,183,433 B2 | 2/2007 | Abbott |

FOREIGN PATENT DOCUMENTS

| JP | 11/050286 | | 2/1999 | |
| WO | WO2006045795 | * | 4/2006 | ............... C01D 3/16 |
| WO | WO2007147222 | * | 12/2007 | ............ C07C 229/76 |

OTHER PUBLICATIONS

Constantinescu, Viscosities, Vapor Pressures, and Excess Enthalpies of Choline Lactate + Water, Choline Glycolate + Water, and Choline Methanesulfonate + Water Systems, JCHEM Eng Data, 2007, 52, pp. 1280-1285.
Fubaya, Bio Ionic Liquids: Room Temperature Ionic Liquids Composed Wholly of Biomaterials, Green Chm., 9:1155-1157, 2007.
International Search Report and Written Opinion in PCT/US2010/061415, Dec. 21, 2010.

* cited by examiner

*Primary Examiner* — Jafar Parsa
*Assistant Examiner* — Amy C Bonaparte

(57) ABSTRACT

A method to synthesize choline salts to be used as inexpensive ingredients for application in ionic liquids or other applications is disclosed.

20 Claims, No Drawings

PROCESS FOR THE SYNTHESIS OF CHOLINE SALTS

TECHNICAL FIELD

This invention relates to a process for the synthesis of choline salts.

BACKGROUND

Choline is conventionally obtained from biological sources with significant impurities and contaminants that are strong discolorants, noxious odor formers, and highly unstable to elevated temperatures. Choline, in the form of choline hydroxide, is most commonly obtained as a very impure viscous liquid with a dark color and strong odor caused from its impurities. These impurities are difficult to remove, even by distillation, and the synthesis of choline salts for industrial applications thus requires significant purification.

Synthesis of choline glycolate using purified glycolic acid reacted with choline hydrogen carbonate, which requires very pure choline hydrogen carbonate, is described by Constantinescu et al in *Chem. Eng. Data,* 52:1280-1285, 2007. Choline glycolate synthesis is also described by Fukaya et al (*Green Chem.,* 9:1155-1157, 2007) wherein an anion exchange column is used to form choline hydroxide followed by addition of glycolic acid. This process requires a very pure, halogenated form of choline, and generates a halogenated waste stream that must be disposed of. These methods are labor intensive and expensive, and are not attractive for commercial-scale operations.

A need thus remains for a process for the high grade synthesis of a wide variety of choline salts that is capable of converting an inexpensive, impure, halogen-free source of choline.

SUMMARY

The inventions disclosed herein include processes for the preparation of choline salts, processes for the preparation of products into which choline salts can be conversed, the use of such processes, and the products obtained and obtainable by such processes.

Features of certain of the processes of this invention are described herein in the context of one or more specific embodiments that combine various such features together. The scope of the invention is not, however, limited by the description of only certain features within any specific embodiment, and the invention also includes (1) a subcombination of fewer than an of the features of any described embodiment, which subcombination may be characterized by the absence of the features omitted to form the subcombination; (2) each of the features, individually, included within the combination of any described embodiment; and (3) other combinations of features formed by grouping only selected features taken from two or more described embodiments, optionally together with other features as disclosed elsewhere herein. Some of the specific embodiments of the processes hereof are as follows:

One such embodiment provides a process for the synthesis of one or more choline salts by providing an aqueous solution of choline; (b) combining the aqueous solution of choline with a hydrophobic organic solvent and an excess of free acid to form a first acidic solution; (c) combining the first acidic solution with one or more alcohols to form a first extraction mixture; (d) separating the first extraction mixture into a lower phase, a middle phase and an upper phase; and (e) recovering the lower phase of the first extraction mixture to provide a first aqueous solution of a choline salt.

In a further alternative embodiment, a process hereof may also include (f) combining the first aqueous solution of choline salt with an excess of free acid and a hydrophobic organic solvent to form a second acidic solution; (g) combining the second acidic solution with at least one alcohol and to form a second extraction mixture; (h) separating the second extraction mixture into a lower phase, a middle phase and an upper phase; and (i) recovering the lower phase of the second extraction mixture to provide a second aqueous solution of a choline salt.

Choline salts are useful in many of the applications in which ionic liquid are used. Ionic liquids describe a class of organic salts containing ionically bound cations and anions that are fluid, typically liquid, in the state of use. Room temperature ionic liquids are liquids composed of ions that are fluid at or below about 100° C. Ionic liquids typically exhibit negligible vapor pressure and low biological toxicity. With increasing regulatory pressure to limit the use of traditional industrial solvents due to environmental considerations such as volatile emissions and aquifer and drinking water contamination, many ionic liquids function as replacements for conventional solvents. Ionic liquids are also useful as absorbents in absorption cooling and heating processes, however, and choline salts would be applicable for that purpose as well.

DETAILED DESCRIPTION

In its various embodiments, this invention provides processes for the syntheses of one or more choline salts.

In one embodiment of the processes hereof, one or more choline salts are synthesized by (a) providing an aqueous solution of choline; (b) combining the aqueous solution of choline with a hydrophobic organic solvent and an excess of free acid to form an acidic solution; (c) combining the acidic solution with one or more alcohols to form an extraction mixture; (d) separating the extraction mixture into a lower phase, a middle phase and an upper phase; and (e) recovering the lower phase of the extraction mixture to provide an aqueous solution of a choline salt.

An aqueous solution of choline suitable for use to form an acidic solution in the processes hereof typically comprises about 20 to 50 wt % of choline dissolved in water. Choline, also known as choline hydroxide (2-hydroxyethyltrimethylammonium hydroxide), is a quaternary amine with the chemical formula. $[(CH_3)_3N^+CH_2CH_2OH][OH^-]$. Choline is not completely stable, and it spontaneously, slowly breaks down to release trimethylamine.

A hydrophobic organic solvent suitable for use to form an acidic solution in the processes hereof is an organic solvent that has limited solubility in water (such as less than about 5% solubility in water), and/or has less than about 5% water solubility in the hydrophobic organic solvent. Examples of hydrophobic organic solvents suitable for use herein include one or more $C_6$ to $C_{10}$ hydrocarbons, both cyclic and acyclic, both aromatic and non-aromatic, and both chlorinated and non-chlorinated. Other hydrophobic organic solvents suitable for use herein include one or more high-boiling-point alkanes, which are alkanes that can easily be handled at ambient conditions as a liquid without pressurization or low temperatures, such as cyclohexane or a mixture of hexanes. A mixture of solvents, i.e. a blend of two or more solvents, may also be used.

An acid suitable for use to form an acidic solution in the processes hereof is an acid that will form a salt with choline, and the acid is typically in the form of a free acid, the free acid being its protonated form. The free acid should be partly water soluble, and should also be substantially non-reactive towards choline and any solvents used in the process.

Acids suitable for use herein include organic acids, which are organic compounds (a carbon-containing compound) having acidic properties, in addition to the stronger mineral acids such as HCl, $H_2SO_4$ or HF. Examples of suitable organic acids include arsonic acids, ascorbic acids, barbituric acids, carbamic acids, carboxylic acids, hydroxamic acids, organosulfur acids (e.g. sulfonic acids), peroxy acids, phosphinic acids, phosphonic acids, picric acids, squaric acids, thiocarboxy acids and uric acids. The most common organic acids are the carboxylic acids, whose acidity is associated with their carboxyl group (—COOH), examples of which include acetic acid, formic acid, lactic acid, pyruvic acid, glycolic acid, propionic acid, isobutyric acid, hydroxy-butanoic acid, hydroxy-propanoic acid and ticrlic acid. The salts and anions of carboxylic acids form carboxylates.

The aqueous solution, the free acid, and the hydrophobic organic solvent can be combined in any order to form an acidic solution. The free acid is used in molar excess compared to the amount of choline used, and suitable ranges for the content of the feed include about 5 to about 20 moles of acid per mole of choline, and more typically about 10 to about 20 moles of acid per mole of choline. In one embodiment, the free acid and the hydrophobic organic solvent are first combined, and then the aqueous solution of choline is added. The mixture can optionally be allowed to phase separate before proceeding.

Next, the alcohol is added to the mixture. The alcohol can be added in aliquots over a period of time, or the entire amount can be added at one time. An alcohol is any organic compound in which a hydroxyl group (—OH) is bound to a carbon atom of an alkyl or substituted alkyl group. The general formula for a simple acyclic alcohol is $C_nH_{2n+1}OH$. The alcohol can be a single compound or a mixture of alcohols, and typically comprises one or more of a $C_1$ to $C_5$ alcohol (i.e. an alcohol containing 1 to 6 carbons), or a $C_1$ to $C_3$ alcohol such as ethanol, propanol or isopropanol. Alcohol is added in an amount such that no additional precipitate is observed after phase separation.

The processes hereof are typically performed below the boiling point and above the crystallization or freezing point of the alcohols, organic solvents and acids used. The processes are typically performed at least about 10° C. lower, or at least about 20° C. lower, than the lowest boiling point of any of the components in the reaction mixture; and are frequently performed close to ambient temperature. Each step in the processes can be performed at the same or a different temperature.

After addition of the alcohol, the mixture is agitated by any suitable means such as stirring or shaking to form a mixture. Agitation is the process step of stirring or shaking until the mixture is sensibly mixed. The mixture is then allowed to phase separate into a lower phase, a middle phase and an upper phase, wherein the multiple phases spontaneously segregate in vertically-stacked layers. Phase separation is the transformation of a homogenous system into two (or more) phases, and can be readily verified visually. The time consumed in the separation that forms these phases may vary according to the particular compounds used and amount of agitation, but is typically 10 to 60 minutes.

The lower aqueous phase contains the choline salt. The lower, aqueous phase containing the choline salt can be utilized as is, or further processed as a solution; or the choline salt can be recovered, isolated and purified from the aqueous solution using methods known in the art such as precipitation, liquid-liquid extraction or washing with acetone. Alternatively, other washing solvents may be used such as methyl ethyl ketone, ethyl acetate, butanol, diethyl ether or methyl t-butyl ether.

As the middle phase, a type of layer forms containing a precipitate, a substantial portion of which frequently contains undesirable impurities originating from the choline source. This precipitate can be removed, if desired, before proceeding to the next step. Additional solvent, acid and/or alcohol can also be added at this point, and the extraction can be repeated one or more times.

The upper phase contains the hydrophobic organic solvent. The upper phase can be recycled as is for use in other extraction cycles, or the upper phase can be purified to recover therefrom a purified solvent, which can be recycled as mentioned above, or can be used in other applications.

In one particular embodiment of the processes hereof, conditions, techniques and reactants suitable for preparing choline carboxylates from choline and a variety of carboxylic acids are described as set forth below. In the processes in which these conditions are used, low molecular weight carboxylic acids such as acetic acid, formic acid, lactic acid, pyruvic acid, propionic acid, iso-butyric acid, hydroxy-butanoic acid and hydroxy-propanoic acid may be used as reactants.

These procedures to prepare choline can be performed, for example, at ambient temperature and pressure. Choline (0.5 mol) is dissolved in water to 50% by weight and is added to a solution of 5% molar excess of carboxylic acid (acid/choline) dissolved in 100 mL of an organic solvent such as cyclohexane in a 1 L flask. The combined solution can be mixed, and after phase separation, small aliquots of an alcohol such as n-propanol can be added while stirring the mixture.

A precipitate comprising impurities from the choline source forms at the interface of the organic and aqueous phases. N-propanol is continually added with mixing until no additional precipitate is observed after phase separation. The aqueous phase containing the product may be separated and retained. Most of the precipitate adheres to the side of the glass flask and separatory funnel, as described above. Methanol may be used to clean the material adhering to the glassware. A second portion of 100 mL cyclohexane and 25 mL n-propanol is added. After more precipitate is formed, the cyclohexane/aqueous separation procedure is repeated. Reaction products can be identified using nuclear magnetic spectroscopy and/or mass spectroscopy.

The advantageous attributes and effects of the processes hereof may be more fully appreciated from a laboratory example, as described below. The process embodiments on which this example is based are representative only and the selection of those embodiments to illustrate the inventions hereof does not indicate that conditions, operating regimes, techniques, materials or reactants not described in this example are not suitable for practicing these processes, or that subject matter not described in this example is excluded from the scope of the appended claims and equivalents thereof.

EXAMPLES

Abbreviations Used

The following abbreviations were used in the examples: "L" means liter, "mol" means mole, "mL" means milliliter, "%" means percent.

Analytical Methods

The reaction products were identified using nuclear magnetic resonance spectroscopy. The NMR instrument, was a Bruker 25, (Bruker Corporation, 40 Manning Park, Billerica Mass.). The NMR solvent was $D_6$-DMSO (99.9%) (Sigma-Aldrich, Milwaukee Wis.).

Materials

Glycolic acid (99%), n-propanol (99.7%), cyclohexane (99.9%) and choline (50% in water) were obtained at the parenthetical purities from Sigma-Aldrich. Phosphorous pentoxide (99.9%) was obtained from Mallinckrodt-Baker (Phillipsburg N.J.).

Example 1

Preparation of Choline Glycolate from Choline and Glycolic Acid

The following steps were performed at ambient temperature and pressure unless noted otherwise. Choline in the amount of 0.5 mol was dissolved in water to 50% by weight. Five percent molar excess of glycolic acid was dissolved in 100 mL cyclohexane in a 1 L The choline solution was added and mixed with the glycolic acid solution. After the mixture was allowed to phase separate, small aliquots of n-propanol were added and the mixture was stirred. A middle phase of precipitate was formed, at the interface of the organic and aqueous phases. N-propanol was continually added with mixing until no additional precipitate was observed after the phases separated, about 50 mL total. The aqueous phase containing the desired choline glycolate product, which was useful as an ionic liquid, was then separated and retained.

A second portion of 100 mL cyclohexane and 25 mL n-propanol was added to the aqueous bottom phase of the previous extraction. When more precipitate was formed, the above extraction separation procedure was repeated.

Excess glycolic acid was removed from the aqueous phase by washing twice with 25 mL of acetone each time. The mixture was poured into a separatory funnel and formed two phases, an acetone top phase and an aqueous bottom phase containing the choline glycolate. The acetone top phase was removed from the aqueous bottom phase containing the choline glycolate. To remove water and residual acetone from the product, 200 mL of n-propanol was added to the aqueous phase, and the excess water was removed by azeotropic evaporation. An additional 100 mL of n-propanol was added, and the evaporation process was continued at 60° C. Remaining water was then removed under high vacuum, using a Welch roughing pump, by gradually raising the temperature from ambient to 60° C. Another 100 mL of n-propanol was added and the evaporation process continued at 50-60° C. Further drying was done by keeping the product under vacuum on the rotary evaporator overnight at room temperature. The product was then placed in a desiccator containing phosphorus pentoxide as a drying agent to remove any residual water. The final yield of choline glycolate obtained was greater than 90%.

Where a range of numerical values is recited or established herein, the range includes the endpoints thereof and all the individual integers and fractions within the range, and also includes each of the narrower ranges therein formed by all the various possible combinations of those endpoints and internal integers and fractions to form subgroups of the larger group of values within the stated range to the same extent as if each of those narrower ranges was explicitly recited. Where a range of numerical values is stated herein as being greater than a stated value, the range is nevertheless finite and is bounded on its upper end by a value that is operable within the context of the invention as described herein. Where a range of numerical values is stated herein as being less than a stated value, the range is nevertheless bounded on its lower end by a non-zero value.

In this specification, unless explicitly stated otherwise or indicated to the contrary by the context of usage, where an embodiment of the subject matter hereof is stated or described as comprising, including, containing, having, being composed of or being constituted by or of certain features or elements, one or more features or elements in addition to those explicitly stated or described may be present in the embodiment. An alternative embodiment of the subject matter hereof, however, may be stated or described as consisting essentially of certain features or elements, in which embodiment features or elements that would materially alter the principle of operation or the distinguishing characteristics of the embodiment are not present therein. A further alternative embodiment of the subject matter hereof may be stated or described as consisting of certain features or elements, in which embodiment, or in insubstantial variations thereof, only the features or elements specifically stated or described are present.

What is claimed is:

1. A process for the synthesis of one or more choline salts, comprising:
   (a) providing an aqueous solution of choline;
   (b) combining the aqueous solution of choline with a hydrophobic organic solvent and an excess of free acid to form a first acidic solution;
   (c) combining the first acidic solution with one or more alcohols to form a first extraction mixture;
   (d) separating the first extraction mixture into a lower phase, a middle phase and an upper phase; and
   (e) recovering the lower phase of the first extraction mixture to provide a first aqueous solution of a choline salt.

2. A process according to claim 1 further comprising:
   (f) combining the first aqueous solution of choline salt with an excess of free acid and a hydrophobic organic solvent to form a second acidic solution;
   (g) combining the second acidic solution with at least one alcohol and to form a second extraction mixture;
   (h) separating the second extraction mixture into a lower phase, a middle phase and an upper phase; and
   (i) recovering the lower phase of the second extraction mixture to provide a second aqueous solution of a choline salt.

3. A process according to claim 1 further comprising isolating the choline salt from the first aqueous solution of choline salt.

4. A process according to claim 2 further comprising isolating the choline salt from the second aqueous solution of choline salt.

5. A process according to claim 1 further comprising recycling the hydrophobic organic solvent for further use in the process.

6. A process according to claim 1 wherein the alcohol comprises at least one $C_1$ to $C_6$ alcohol.

7. A process according to claim 1 wherein the alcohol comprises ethanol, propanol or isopropanol.

8. A process according to claim 1 wherein the hydrophobic organic solvent comprises a high-boiling-point alkane.

9. A process according to claim 1 wherein the hydrophobic organic solvent comprises cyclohexane.

10. A process according to claim 1 wherein the free acid comprises an organic acid.

11. A process according to claim 1 wherein the free acid is selected from the group consisting of acetic acid, formic acid, lactic acid, pyruvic acid, glycolic acid, propionic acid, isobutyric acid, hydroxyl-butanoic acid, hydroxyl-pentanoic acid and tiglic acid.

12. A process according to claim 1 wherein the free acid comprises glycolic acid.

13. A process according to claim 1 wherein the free acid comprises hydrochloric acid.

14. A process according to claim 1 wherein the hydrophobic organic solvent comprises one or more $C_6$ to $C_{10}$ hydrocarbons.

15. A process according to claim 1 wherein the hydrophobic organic solvent has less than about 5% solubility in water, and/or has less than about 5% water solubility therein.

16. A process according to claim 1 wherein the free acid is selected from the group consisting of HCl, $H_2SO_4$, HF, an arsonic acid, an ascorbic acid, a barbituric acid, a carbamic acid, a carboxylic acid, a hydroxamic acid, an organosulfur acid, a peroxy acid, a phosphinic acid, a phosphonic acid, a picric acid, a squaric acid, a thiocarboxy acid and a uric acid.

17. A process according to claim 1 wherein the free acid is provided in an amount of about 5 to about 20 moles of acid per mole of choline.

18. A process according to claim 1 that is performed below the boiling point and above the crystallization or freezing point of the alcohol(s), organic solvent(s) and/or acid(s) used therein.

19. A process according to claim 1 wherein the middle phase comprises a layer; and/or the upper phase comprises the hydrophobic organic solvent.

20. A process according to claim 1 further comprising applying a washing solvent to recover, isolate and/or purify the choline salt from the aqueous solution.

* * * * *